United States Patent [19]

Ozero et al.

[11] Patent Number: 4,921,681
[45] Date of Patent: May 1, 1990

[54] ETHYLENE OXIDE REACTOR

[75] Inventors: Brian J. Ozero, New York; Stanley D. Becker, Hewlett, both of N.Y.

[73] Assignee: Scientific Design Company, Inc., Little Ferry, N.J.

[21] Appl. No.: 178,928

[22] Filed: Apr. 7, 1988

Related U.S. Application Data

[62] Division of Ser. No. 75,227, Jul. 17, 1987, abandoned.

[51] Int. Cl.$^5$ .............................................. B01J 8/06
[52] U.S. Cl. .................................... 422/197; 165/159; 165/173; 165/178; 422/201; 422/205; 549/534
[58] Field of Search ...................... 422/197, 201, 205; 165/159, 173, 178; 549/534

[56] References Cited

U.S. PATENT DOCUMENTS

| | | | |
|---|---|---|---|
| 1,589,632 | 6/1926 | Downs | 422/201 X |
| 2,029,604 | 2/1936 | Bayer et al. | 422/197 X |
| 2,098,148 | 11/1937 | Jarl | 422/201 |
| 2,660,609 | 11/1953 | Robeson et al. | |
| 3,431,083 | 3/1969 | Bergstrand | 422/197 X |
| 3,566,961 | 3/1971 | Lorenz et al. | 422/197 X |
| 4,061,659 | 12/1977 | Nielson et al. | 549/534 |
| 4,203,906 | 5/1980 | Takada et al. | 165/159 X |

FOREIGN PATENT DOCUMENTS 1449091 4/1973 United Kingdom .
1449092 4/1973 United Kingdom .

OTHER PUBLICATIONS

Japanese Patent Abstract 30553B/16 (Pat. No. 3240879, 3-9-78).
Japanese Patent Abstract 21216C/12 (Pat. No. 1920680, 2-9-80).

Primary Examiner—Michael S. Marcus
Assistant Examiner—Jill Johnston
Attorney, Agent, or Firm—Kenneth H. Johnson

[57] ABSTRACT

Improved performance is obtained in a multi-tube reactor for oxidation of ethylene to ethylene oxide by providing a distribution zone for the coolant located downstream of the catalyst and a contiguous cooling zone. The effluent gases from the oxidation are cooled in the cooling zone by a fluid, which has been only slightly preheated and distributed uniformly in the distribution zone by contact with tubes in which the effluent gases are in low-turbulence flow. Uniform distribution of the coolant provides substantially equal cooling of the effluent gases in each tube, thus minimizing the variation in effluent gas temperature among the tubes. Preferably, the tubes in the cooling section are packed with inert particles to facilitate heat transfer, while the tubes are empty in the distribution section to reduce heat transfer.

10 Claims, 2 Drawing Sheets

ETHYLENE OXIDE REACTOR

This application is a division of Ser. No. 075,227 filed Jul. 17, 1987, now abandoned.

BACKGROUND OF THE INVENTION

The invention relates generally to the design of tubular reactors for carrying out exothermic chemical reactions. In a preferred mode, it relates to the process for catalytically oxidizing ethylene to ethylene oxide and reactors useful therein.

Generally, the ethylene oxidation reaction is carried out in multi-tube reactors in which the catalyst is disposed inside the tubes and the exothermic heat of reaction is removed by a fluid circulating on the outside of the tubes. The gases fed to the catalyst tubes contain ethylene and oxygen, along with other gases such as nitrogen, carbon oxides, and argon. The conditions under which the reaction takes place will affect the detailed design of the equipment, but they do not critically influence the effectiveness of the present invention.

In commercial reactors, the gases leave the reaction tubes at a higher temperature than the coolant on the shell side. The temperature of the gases from each tube will depend upon the heat released during the oxidation and the amount of heat removed by the coolant. Operating conditions will be adjusted to produce the best results. As the catalyst declines in activity the outlet temperature is increased.

The prior art has been concerned with the methods by which the effluent gases are cooled after the reaction. At the outlet of the catalyst bed, the gas temperature may be about 230° to 300° C., depending upon various factors. At these temperatures, it is important to cool the gases promptly to minimize the loss of ethylene oxide by isomerization to acetaldehyde and, particularly as the temperature increases, to avoid burning of the hydrocarbons to carbon oxides and water. The burning may take place in a rapid and localized manner causing excessive pressures and temperatures, thus forcing corrective actions to be taken which cause loss of ethylene oxide production and in extreme cases endangering the equipment. Thus, if the temperature of the effluent gases can be lowered quickly, operation at the most efficient conditions is made safer and more stable.

Cooling a large number of tubes uniformly has been found to be difficult. In addition, the heat removed must be usefully employed if the most efficient operation is to be obtained.

In British Patents Nos. 1,449,091 and 1,449,092, it is shown to be typical to exchange heat between the effluent gases and the incoming feed gases in an external heat exchanger. The disadvantages of such designs are discussed in connection with disclosure of the patentees design in which the effluent gases provide heat to the feed gases via a closed heat exchange loop. The feed gases are heated in a contiguous section of the reactor tubes which contain an inert packing to facilitate heat transfer. The effluent gases may be sent to an external heat exchanger, which preferably contains no solid packing, or may give up heat and cool to below 150° C. in a second contiguous section of the tubes, which it is said, may be either packed or not. Actually, use of packing in this section is considered likely since heat transfer in empty tubes is inefficient as will be seen.

As pointed out in U.S. Pat. No. 4,061,659 use of packing in the cooling zone is desirable since it reduces the residence time at high temperatures and consequently reduces the loss of ethylene oxide. The patentee stated that it is important to minimize the surface area of the inert packing to limit losses of ethylene oxide. This appears consistent with earlier patents which suggested such high-surface area solids as alumina and silica be used to isomerize alkylene oxides (see U.S. Pat. No. 2,660,609). Another reason for using inert packing in these tubes is to maintain the high velocities and turbulence needed for effective heat removal. Without packing, the effluent gases would slow down and the tube-side heat transfer coefficient would be reduced by about 80–90° %, thereby drastically reducing cooling of the reaction gases. This would require additional tube length and undesirable residence time to provide the needed cooling.

The use of packing in contiguous cooling sections is shown also in Japanese Published Applications No. 32408/79 and 19206/80.

Obtaining uniform distribution of the cooling fluid is important if each tube is to be cooled to substantially the same temperature. While the bulk temperature of the effluent gases may be lowered adequately, it is undesirable for some tubes to be cooled below the bulk temperature, while others remain at too high a temperature. Ideally, each tube should be cooled equally by a stream of cooling fluid having the same temperature. The present invention relates to that objective.

SUMMARY OF THE INVENTION

The oxidation of ethylene by molecular oxygen to ethylene oxide over a supported silver catalyst is conventionally carried out in a reactor having a large number of tubes containing the catalyst in contact with a circulating fluid to remove the exothermic heat of reaction. Reduced losses of ethylene oxide and a lower risk of uncontrolled and localized burning at the outlet of the reactor may be obtained by a controlled cooling of the effluent gases in a section of the tubes packed with inert particles and disposed downstream of the catalyst. Uniform cooling of the effluent gases is obtained according to the invention by extending the tubes into a separate distribution zone where the gases are in low-turbulence (i.e. near-laminar) flow to minimize cooling and allow uniform distribution of coolant around the tubes with minimal temperature increase. Preferably, the inert packing typically used in the cooling zone will be omitted. Alternatively, the distribution zone may contain some supporting materials, provided that low-turbulence flow is retained. The heat transfer coefficient on the inside of the tubes should be no greater than about 200 kcal/hr-m$^2$-° C., preferably no greater than 150 kcal/hr-m$^2$-° C., most preferably no greater than 80 kcal/hr-m$^2$-° C.

In a preferred application, the effluent gases will be cooled about 20° to 35° C. in the cooling zone, but no more than about 6° C. in the distribution zone, thereby permitting a uniform cooling of the effluent gases and minimizing temperature variations among the many tubes. The heat transfer coefficient of the effluent gases in the packed cooling zone preferably will be about 485 to 560 kcal/hr-m$^2$-° C. and the heat transfer coefficient for the coolant will be about 300 to 450 kcal/hr-m$^2$-° C., making the overall heat transfer coefficient about 185–250 kcal/hr-m$^2$-° C. With low-turbulence flow in the distribution zone, the corresponding heat transfer coefficients would be about 50 to 70 kcal/hr-m$^2$-°C. inside the tubes, 300 to 450 kcal/hr-m$^2$-°C. for the coolant, giving an overall coefficient of 40 to 60 kcal/hr-m$^2$-°C. The temperature variation among the tubes may be kept at as little as about 2°C.

In a preferred embodiment the coolant is water, which enters near the gas outlet and flows both radially inward and parallel to the tubes in the distribution zone. Then, the water flows through annular openings in a baffle separating the distribution and cooling zones and thereafter provides cooling for the effluent gases. Upon leaving the cooling zone, the heated water enters the reaction section where it mixes with recirculating boiler feed water and removes the exothermic heat of reaction by boiling.

In another embodiment, the invention comprises a tubular reactor for vapor phase exothermic reactions where a set of catalyst-containing tubes is disposed between tubesheets and surrounded by a shell, and thus operates as a heat exchanger to remove the heat of reaction. Effluent gases from the reaction are passed into a contiguous section of the tubes, which forms a distribution zone where flow of the gases creates low-turbulence and minimal cooling is done. Variation of the effluent gas temperatures is minimized. A heat transfer fluid is only slightly heated and uniformly distributed in the distribution zone to permit uniform cooling of the effluent gases in the cooling zone of the reactor.

DESCRIPTION OF THE PREFERRED EMBODIMENTS

The oxidation of ethylene to ethylene oxide is a well-known industrial process. Typically, ethylene is fed into a gas stream which recirculates through a reactor where the ethylene is partially converted and then through cooling and scrubbing facilities where the ethylene oxide is removed by absorption in water. After removal of the ethylene oxide product, the gas stream is compressed and recycled to the reactor. Carbon oxides, by-products of the oxidation, are removed from the recycle gas stream by purging or scrubbing. Only about 10-20% of the ethylene feed is converted, with a selectivity to ethylene oxide of about 70-80%, the remainder being burned to carbon oxides and water. The recirculating gas stream thus contains a significant amount of ethylene and enough is added to replace the amount being converted. Various inerts may be employed as ballast gas for the reaction as are well-known in the art. For example, nitrogen, methane, and others which do not have an adverse effect on the oxidation of ethylene to ethylene oxide. Moderators, such as chlorinated hydrocarbons, are used in small quantities to improve the selectivity to ethylene oxide.

Figure 1:
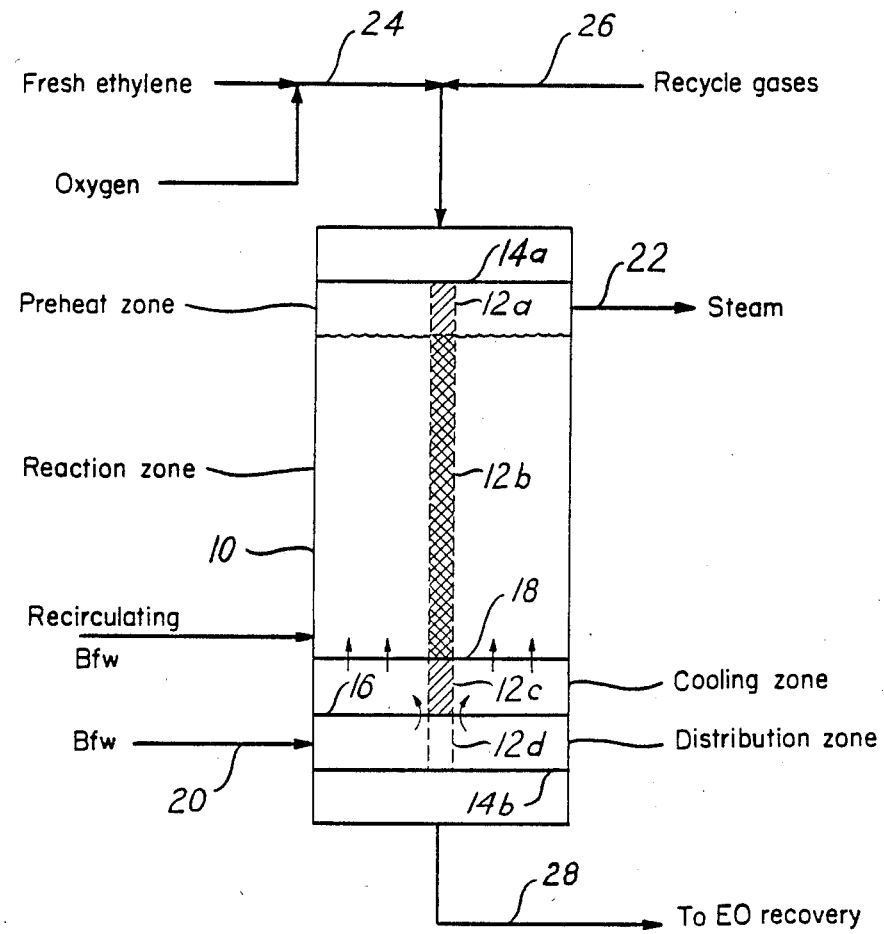
FIG. 1 represents a multi-tube reactor constructed and operated in accordance with the invention.

The construction of the oxidation reactor may be seen by reference to FIG. 1 which, although it is intended to show a reactor designed according to the present invention, can be used to describe the conventional construction as well. Fresh ethylene feed 24 is shown joining the recycle gas stream 26 and entering the reactor 10. The combined gases enter the many catalyst-containing tubes represented by tube 12, which are oriented vertically and, being surrounded by a shell, are similar to a shell and tube heat exchanger. These tubes are usually about 20 to 40 mm in internal diameter. They are sealed into inlet and outlet tube sheets 14a and b. The shell side of the reactor 10 contains a circulating fluid which removes the heat of reaction. Various fluids have been used, such as water, Mobiltherm, Dowtherm, and kerosene, but the present invention is particularly suited to the use of boiling water. Steam produced by boiling water in the shell is continuously removed near the top of the reactor and then used for various purposes, such as for preheating recycle gas. In the present drawing, the steam preheats the incoming feed gases in a section of each tube 12a which is packed with an inert solid to facilitate heat transfer. The gases are brought to near the reaction temperature, typically in the range of 200 to 240°C. The preheat section is not required by the invention and the function may be provided by an external heat exchanger. The gases pass down through the section of each tube 12b, which contains the catalyst, typically a supported silver catalyst of the type well-known in the art. Such catalysts typically convert ethylene with a selectivity to ethylene oxide of about 70-80% but with a rather low conversion of only 10-20%. Heat released by the desired reaction, plus the substantial heat of combustion which also occurs, passes through the tube walls and boils the water on the shell side. After passing through the catalyst section 12b, which may be 6 to 10 meters long, the hot effluent gases are ready to be cooled and the ethylene oxide recovered, typically in a contiguous section 12c of each tube packed with an inert solid, as is familiar from the prior art discussed earlier.

As explained before, some of the ethylene oxide produced may be lost by isomerization to acetaldehyde and/or oxidation to carbon oxides and water. Once the gases leave the catalyst it is highly desirable to quickly cool them to avoid losses of ethylene oxide. In addition, uncontrolled burning may occur where large amounts of hot reaction gas are present, which forces adjustments to be made to the reactor operation which result in a loss of ethylene oxide production and may cause damage to the equipment.

In the drawing, boiler feed water 20 is used to cool the tubes. However, while in conventional heat exchangers the bulk temperatures of the fluids are sufficient to govern the design, in the ethylene oxide reactor, it is important to minimize variation of temperatures from tube-to-tube. The practical difficulty may be appreciated if it is understood that a large commercial reactor may have up to 12,000 tubes and be in excess of 5 meters in diameter. According to the invention, uniform rapid cooling is obtained by providing an annular opening around each tube as it passes through baffle 16. A stream of water passes upwardly from the space below (to be described) and contacts each tube substantially countercurrently, the water being in laminar flow. After providing cooling the streams of water are passed through baffle 18 to the reaction area where boiling occurs, as previously explained. Each stream of water ideally will be at substantially the same temperature as it passes through baffle 16 in order to assure that the amount of cooling provided to the effluent gases in each tube will be the same as that of the other tubes. A water inlet cannot be conveniently provided for each tube. Therefore, even with multiple inlets disposed around the circumference of the cooling zone, the bulk of the water will be heated by the outer tubes and thus be too hot to provide the needed cooling to the inner tubes. It is a feature of the invention to provide a cooling water stream at nearly the same temperature to each tube. This is done by forming a water distribution zone in which minimal cooling is done.

To achieve this, a contiguous section 12d of each tube downstream of the packed cooling section 12c preferably is left empty. The effluent gases slow down drastically in the unpacked section 12d, reducing the heat transfer on the tube side to about 10% of the value in the packed section 12c. The resulting low-turbulence flow reduces the heat transfer coefficient on the tube side. The term "low-turbulence" flow will be understood by those skilled in the art to refer to fluid velocities in the lower portion of the turbulent flow regime, that is, approaching laminar flow. There, the heat transfer coefficient is sharply reduced from that created by highly turbulent flow, which is usually employed when good heat transfer is desired. According to our invention, the tube-side heat transfer coefficient will be no more than about 200 kcal/hr-m$^2$-° C., preferably no more than about 150 kcal/hr-m$^2$-° C., most preferably less than 80 kcal/hr-m$^2$-° C. In a preferred embodiment, the heat transfer coefficient would be about 50 to 70 kcal/hr-m$^2$-° C. Water is distributed in laminar flow on the shell side, thus limiting heat transfer markedly. The heat transfer coefficient of the coolant water typically will be about 300 to 450 kcal/hr-m$^2$-° C. The boiler feed water 20 will enter the distribution zone at a number of points about the outside of the shell and pass radically inward toward the center of the reactor with only a little cooling of the gas. The flow of water around each tube through the passageway in the baffle 16 may be controlled by the size of the openings. Properly sized, the distribution zone can limit temperature variation between the tubes to as little as about 2° C., compared to a conventional cooling zone, which could provide temperature variations of about 15 to 20° C. Minimizing such temperature variations will be an important advantage to those wishing to operate a reactor at high temperatures while avoiding uncontrolled burning and its associated effects.

Figure 1A:
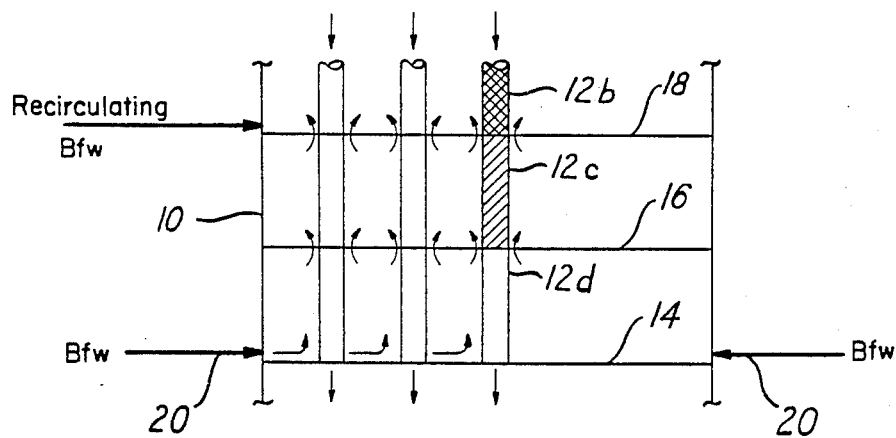
FIG. 1a is an enlarged view of a portion of the the reactor of FIG. 1.

The lower portion of the reactor is shown in the enlarged drawing of FIG. 1A. Boiler feed water (bfw) enters through several entry nozzles disposed around the circumference of the reactor to assure uniform flow across the tubes. The water flows toward the center of the bundle of tubes, represented here by only three tubes for clarity. A portion of the water passes upwardly through the annular openings between each tube (12) and baffle 16. The velocity is kept low to provide a poor heat transfer coefficient on the shell side of the tubes, which cooperates with the low velocity on the inside of the tubes to limit the transfer of heat from the process gases to the water—the opposite of the usual design of a cooling section. The water flows upward along the tubes in the cooling section and exits through annular spaces between the tubes and baffle 18 to enter the reaction section, where boiling occurs to remove the heat generated. Section 12b is packed with catalyst, while section 12c is packed with solid particles to facilitate the desired cooling. Section 12d is left empty or contains only such solids as will not significantly improve heat transfer.

The practical application of the invention will be seen in the following examples.

EXAMPLE 1

The reactor 10 in the FIG. 1 is shown schematically but in a typical commercial configuration is 4 meters inside diameter containing 5160 tubes, each having an internal diameter of 31.3 mm. The reactor shell is oriented vertically with the tubes 12 distributed substantially uniformly about the cross sectional area. Each tube is sealed into inlet and outlet tube sheets 14a and b. Internal baffles 16 and 18 divide the lower portion of the shell side into the distribution and cooling zones. Baffle 16 and the outlet tube sheet 14b define the distribution zone, while baffle 16 and baffle 18 define the cooling zone. Boiler feed water 20 having a temperature of 168° C. is supplied to the distribution zone where it is distributed with minimal heating so that a water stream is passed through an annular opening in baffle 16 where each tube passes through the baffle. The external diameter of the tube is 38.1 mm and the diameter of the opening is about 38.9 mm, leaving an opening sufficient to provide the nearly uniform distribution of boiler feed water which is desired. The water passes upwardly in substantially laminar flow adjacent to the tube with which its associated, receiving heat to raise the temperature to near the boiling point. The main recirculating boiler feed water is supplied above baffle 18 to the main heat removal section defined by the inlet tube sheet 14a and baffle 18 where the water boils and is removed by steam via line 22. The length of each tube is 10.6 meters of which 8 meters is filled with a supported silver catalyst on a 6–8 mm support which is sized to provide good contacting, but without unduly restricting the flow of gases passing through the tube. The preheat zone is approximately 0.6 meters long, which can be varied depending on the water level carried on the shell side. Preheat is supplied to the feed gases in an area which is packed with a inert material similar to that used as catalyst support.

The cooling zone between baffles 16 and 18 is 1.5 meters long and the tubes are filled with inert particles similar to those employed in the preheat just described. The purpose of including an inert material in both zones is to facilitate transfer of heat to or from fluids passing on the shell side. That is, to receive heat from steam in the preheat zone and to give up heat to boiler feed water in the cooling zone. The section of each tube extending into the distribution zone is, according to the invention, preferably left free of any inert materials which would assist heat transfer. Any solid material in the tube 12d should not disturb flow of the gases significantly in order to obtain the desired low-turbulence. The gases on the inside of the tubes slow down from a velocity of about 3 meters/second through the spaces between the inert particles in the cooling zone to 1.0 meters/second in the empty distribution zone. Thus, the heat transfer sufficient is reduced by about 90%. The velocity of boiler feed water on the shell side of the distribution zone is also kept low (i.e., in sub-turbulent flow), in order to minimize the heat transfer on the shell side. Thus, the distribution zone serves to divide the boiler feed water into multiple water streams, one for each tube, which flow vertically in the cooling zone and cool the effluent gases.

Typical operation of the reactor in the oxidation of ethylene may be described as follows. Fresh feed containing ethylene and oxygen flows through line 24 and joins the recycle gases in line 26, having the composition 15–30% ethylene, 7–9% oxygen, 5–15% $CO_2$, 5-15% argon with the balance nitrogen and methane. The temperature and pressure of the combined feed stream is about 180° C. and 22 kg/cm² gauge. The gases enter the open portion above the inlet tube sheet 14a and pass into the reactor tubes 12, where the gases are preheated 12a to about 240° C. The reaction begins at the upper portion of the reaction zone 12b. The heat of reaction is removed by boiling water kept at a temperature of about 240° C. and 34.5 kg/cm² gauge, typically by pressure controls not shown. Temperature of the effluent gases at the inlet of the cooling zone (i.e. baffle 18) is 245° C. The gases pass downwardly in each tube 12c countercurrently to boiler feed water flowing upward from the distribution zone, thereby cooling the gases to about 235° C., while heating the boiler feed water to nearly 240° C. The temperature of the effluent gases varies very little from tube to tube because the water flow has been distributed proportionally to the gas flow and the water temperature can only rise to the boiling point which limits heat transfer. The gases enter the distribution section where, owing to the intentionally poor heat transfer, further cooling of about 0.3 to 3.5° C. occurs in 12d. The boiler feed water is distributed proportionally to the gas flow by passing through the annular openings between the tubes and the horizontal baffle 16. The temperature rises from 168° C. at the inlet to about 171° C. near the shell and to about 189° C. at the center of the reactor. The gases are cooled nearly equally as already indicated. The gases exit each tube into the outlet portion of the reactor where they are mixed and then removed via line 28 for recovery of ethylene oxide (not shown).

EXAMPLE 2

Figure 2:
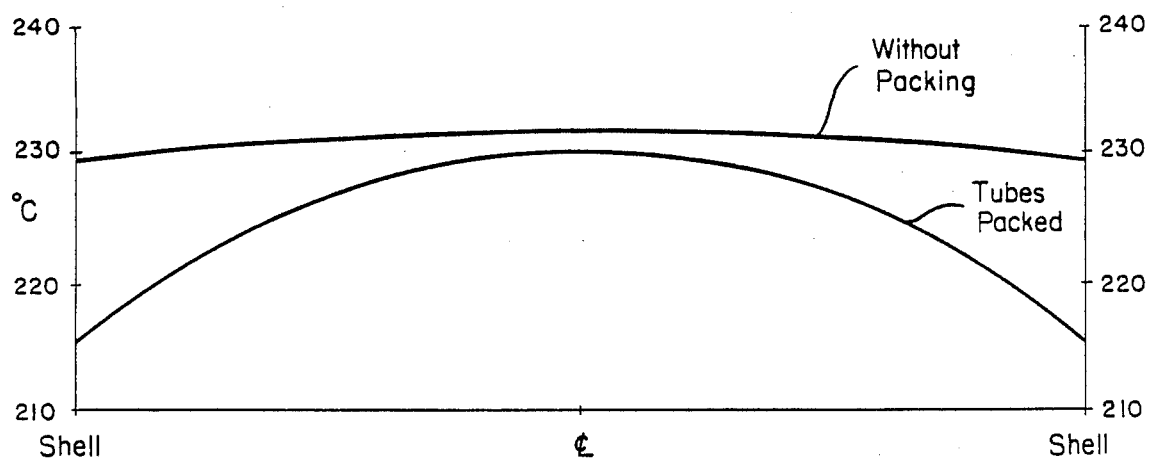
FIG. 2 is a graph illustrating the performance of a typical reactor according to the invention.

The plot in FIG. 2 shows the reactor performance which is obtained according to the invention as compared with same reactor design, and differing only in that the tubes in the distribution section are packed with an inert material instead of being empty. The effect is to cause the temperature variation between the gas at the shell and at the centerline to be about 14.3° C. as compared with only about 3.8° C. when the tubes are empty. If the effluent gases enter the distribution section at 235° C. as in Example 1, the gas in tubes near the shell is cooled to about 215° C. while in tubes near the centerline the temperature is about 230° C.

The large difference in temperature resulting from merely packing the tubes in the distribution section and thereby increasing the heat transfer coefficient is highly undesirable. If a particular maximum temperature is not to be exceeded, say 230° C. in this example, then the operating temperature in the reactor would be limited to about 10° C. lower value than with the invention. Potentially, catalyst life is shortened since the temperature cannot be increased as much as desired to counter loss in catalyst activity as it ages. More importantly, the reactor is subjected to a greater degree to the risks associated with excessively high outlet temperatures, that is, to loss of production and potential equipment damage.

Although the examples above show temperatures typical of start-of-run conditions with fresh catalyst, it will be understood that comparable differences in temperatures will be found when the catalyst has aged. In fact, since temperatures are on the average higher at that time, the risks are greater and a reactor constructed according to the invention has even greater advantages.

We claim:

1. In a process for the catalytic oxidation of ethylene with molecular oxygen to ethylene oxide in a fixed bed reactor wherein a supported silver catalyst is disposed in multiple tubes surrounded by a fluid which removes the exothermic heat of reaction and said tubes have a contiguous cooling gas cooling zone containing inert particles disposed downstream of said catalyst having a first overall heat transfer coefficient to provide rapid cooling of the effluent gases, the improvement comprising providing a contiguous coolant distribution zone downstream of said cooling zone in which the effluent gases are in low-turbulence flow to provide a second overall heat transfer coefficient substantially lower than said first overall heat transfer coefficient which prevents the temperature of the coolant entering said distribution zone from increasing substantially as it passes over said tubes before flowing into said cooling zone.

2. The process of claim 1 wherein the heat transfer coefficient inside the tubes in the distribution section is no more than about 150 kcal/hr-m²-° C.

3. The process of claim 1 wherein the heat transfer coefficient inside the tubes in the distribution section is no more than about 80 kcal/hr-m²-° C.

4. The process of claim 3 wherein the heat transfer coefficient outside the tubes in the distribution section is in the range of about 300 to 450 kcal/hr-m²-° C.

5. The process of claim 1 wherein said coolant is water.

6. The process of claim 5 wherein said heat of reaction is removed by boiling water.

7. In a process for the catalytic oxidation of ethylene to ethylene oxide in a fixed bed reactor wherein a supported silver catalyst is disposed in multiple tubes surrounded by a flowing fluid which removes the exothermic heat of reaction and said tubes have a contiguous cooling zone downstream of said catalyst having a first overall heat transfer coefficient to provide rapid cooling of the effluent gases, the improvement comprising providing a contiguous coolant distribution zone downstream of said cooling zone in which the effluent gases are in low-turbulence flow to provide a second overall heat transfer coefficient substantially lower than said first overall heat transfer coefficient which prevents the temperature of the coolant radially entering said distribution zone from increasing substantially as it passes over said tubes before beginning axial flow into said cooling zone.

8. The process according to claim 7 wherein said first overall heat transfer coefficient is in the range of 185 to 250 kcal/hr.-m²-° C. and said second overall heat transfer coefficient is in the range of 40-60 kcal/hr.-m²-° C.

9. The process according to claim 8 wherein the heat transfer coefficient inside the tubes in said cooling zone is in the range of 485 to 560 kcal/hr.-m²-° C. and the heat transfer coefficient outside the tubes in said cooling zone is in the range of 300 to 450 kcal/hr.-m²-° C.

10. The process according to claim 8 wherein the heat transfer coefficient inside the tubes in said coolant distribution zone is in the range of 50 to 70 kcal/hr.-m²-° C. and the heat transfer coefficient outside the tubes in said coolant distribution zone is in the range of 300 to 450 kcal/hr.-m²-° C.

* * * * *